US012605448B2

(12) United States Patent

Schwendeman et al.

(10) Patent No.: US 12,605,448 B2

(45) Date of Patent: Apr. 21, 2026

(54) POROUS SELF-HEALING POLYMER MATRIX FOR ENCAPSULATION OF ACTIVE MACROMOLECULES AND METHODS

(71) Applicant: THE REGENTS OF THE UNIVERSITY OF MICHIGAN, Ann Arbor, MI (US)

(72) Inventors: Steven P. Schwendeman, Superior Township, MI (US); Jason Albert, Ann Arbor, MI (US); Rae Sung Chang, East Brunswick, NJ (US); George A. Garcia, Dexter, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1068 days.

(21) Appl. No.: 17/627,878

(22) PCT Filed: Jul. 20, 2020

(86) PCT No.: PCT/US2020/042824

§ 371 (c)(1),
(2) Date: Jan. 18, 2022

(87) PCT Pub. No.: WO2021/016211

PCT Pub. Date: Jan. 28, 2021

(65) Prior Publication Data

US 2022/0257769 A1     Aug. 18, 2022

Related U.S. Application Data

(60) Provisional application No. 62/876,373, filed on Jul. 19, 2019.

(51) Int. Cl.
| | |
|---|---|
| *A61K 47/34* | (2017.01) |
| *A61K 38/19* | (2006.01) |
| *A61K 47/36* | (2006.01) |

(52) U.S. Cl.
CPC ............ *A61K 47/36* (2013.01); *A61K 38/193* (2013.01); *A61K 47/34* (2013.01)

(58) Field of Classification Search
CPC ...... A61K 47/36; A61K 38/193; A61K 47/34; A61K 9/1647; A61K 9/1694; A61K 9/0024
See application file for complete search history.

(56) References Cited

U.S. PATENT DOCUMENTS

| | | |
|---|---|---|
| 2008/0131478 A1 | 6/2008 | Schwendeman et al. |
| 2012/0288537 A1 | 11/2012 | Schwendeman et al. |
| 2015/0125531 A1* | 5/2015 | Schwendeman ....... A61K 38/09 |
| | | 424/78.17 |
| 2015/0164805 A1 | 6/2015 | Schwendeman et al. |

FOREIGN PATENT DOCUMENTS

| | | |
|---|---|---|
| WO | WO-99/00670 A1 | 1/1999 |
| WO | WO-2011/088229 A2 | 7/2011 |
| WO | WO-2015/070172 A1 | 5/2015 |

OTHER PUBLICATIONS

International Application No. PCT/US2020/042824, International Search Report and Written Opinion, mailed Nov. 3, 2020.

* cited by examiner

*Primary Examiner* — Jessica Worsham

(74) *Attorney, Agent, or Firm* — MARSHALL, GERSTEIN & BORUN LLP; Andrew M. Lawrence

(57) ABSTRACT

The present disclosure relates to a porous self-healing polymer matrix for encapsulation of active macromolecules and a method of manufacturing said porous self-healing polymer matrix for a drug delivery system for a macromolecule.

21 Claims, 4 Drawing Sheets

POROUS SELF-HEALING POLYMER MATRIX FOR ENCAPSULATION OF ACTIVE MACROMOLECULES AND METHODS

CROSS REFERENCE TO RELATED APPLICATIONS

This application is the U.S. national phase of PCT Application No. PCT/US20/42824, filed on Jul. 20, 2020, which claims the benefit of U.S. Provisional Application No. 62/876,373, filed Jul. 19, 2019, the entire disclosures of which are hereby incorporated by reference in their entirety.

FIELD OF THE INVENTION

The present technology relates to a porous self-healing polymer matrix with high encapsulation efficiency for an active macromolecule such as a protein or peptide.

BACKGROUND

Injectable, biodegradable polymeric particles, such as microspheres, provide a means to deliver and control the release of molecules such as drugs, proteins, peptides and vaccine antigens. Once injected, the biodegradable polymeric particles can release the molecule over the course of hours, days or even extended periods such as weeks or months, thus eliminating the need for daily injections, and thereby improving patient acceptance and compliance. Controlled release of a protein antigen can reduce the number of doses in an immunization schedule and optimize the desired immune response by selectively targeting the antigen to the targeted antigen presenting cells.

An array of biodegradable polymers have been used for the microencapsulation and delivery of macromolecules. For example copolymers of lactic acid and glycolic acid (PLGA) are biodegradable and biocompatible, and have been used in pharmaceutical products and medical devices that have been approved by the U.S. Food and Drug Administration. PLGA polymer systems are presently used in commercially available, controlled-release delivery systems for peptides including leuprolide acetate (Lupron Depot™), octreotide acetate (Sandostatin LAR™), and goserelin acetate (Zoladex™ implant).

Injectable, biodegradable polymeric particles are of intense interest for controlled-release, injectable depots capable of the slow, complete release in vivo of proteins in their native (active) state because they are capable of sequestering these macromolecules and protecting them from enzymatic or other degradation before they are released. Nevertheless, significant obstacles have been encountered. Of concern is the stability of proteins and peptides during encapsulation. Methods for encapsulating macromolecules in biodegradable polymers can involve harsh processing conditions, including exposure to organic solvents, excess heat, and homogenization methods such as mixing, sonication and high-speed agitation. These methods alone or in combination can denature and/or destabilize proteins and other macromolecules. Drying and micronization of a macromolecule prior to encapsulation may further destabilize the macromolecule.

Hydrophilic macromolecules, including many proteins, cannot readily diffuse through a hydrophobic polymer phase of many biodegradable polymers such as PLGA. The release of encapsulated protein drugs from a PLGA matrix, therefore, requires the hydrophilic macromolecules to diffuse through water-filled pores or channels. As a result, protein release from PLGA microspheres often exhibits tri-phasic behavior. In the first phase, protein on the surface or having immediate access to the surface of the microspheres (i.e., in open pores) is released rapidly, providing an initial burst release. Second, a time lag occurs, as the protein within the interior of the microsphere cannot diffuse through the polymer phase. Third, a continuous release of protein occurs due to polymer erosion that causes more pores and channels to be formed allowing protein to be released from previously isolated pores or chambers within the microsphere. "Microsphere" refers to a solid particle (excluding gel, liquid and gas), having an average geometric particle size of less than 1 mm, for example 200 microns or less, 100 microns or less, 75 microns or less, or greater than 10 microns, greater than 25 microns, etc. Average geometric particle size is measured by, for example, light microscopy and/or use of a mechanical sieve. In some embodiments, the average geometric particle size can be in a range of about 10 microns to about 100 microns, for example, about 15 microns to about 70 microns or about 60 microns to about 95 microns.

Encapsulation methods using preformed microspheres comprising self-healing polymers have been developed for peptides, proteins, DNA, siRNA, and other macromolecules (U.S. Pat. No. 8,017,155, hereby incorporated by reference in its entirety). The macromolecule is loaded into a preformed, porous microsphere, preferably having an interconnected pore network having access to an external aqueous solution. Loading of the microspheres is performed in an aqueous solution of the macromolecules at a temperature that is below the glass transition temperature ($T_g$) of the microsphere polymeric matrix so that the macromolecule is taken up into the pores of the polymeric matrix. Next, the temperature is raised above the $T_g$ so that the polymer pores close (heal), encapsulating the macromolecule. PLGA advantageously has a hydrated glass transition temperature at a temperature range at which many proteins are stable in aqueous solutions with or without protein stabilizers for appreciable lengths of time to allow pore healing (closure). However, plasticizers have also been added to PLGA to reduce the healing temperature to 37° C. Alternatively, other methods besides temperature change can be used to close the pores. For example, exposure to a solvent, such as alcohol vapor, can be used to facilitate pore closure (self-healing) of the polymer matrix. Using this methodology, loading of about 10% w/w of active protein agent to PLGA can be achieved.

The foregoing passive encapsulation methods thus rely on equilibration of the peptide or protein to be delivered between the solution outside the polymer phase or microsphere, and the aqueous pores within the microsphere. Passive encapsulation typically requires high concentrations of the macromolecule (>50-100 mg/mL) in order to achieve adequate loading. This elevated concentration requirement could prohibit encapsulation of macromolecules with moderate to low solubility. In addition, passive encapsulation generally results in low encapsulation efficiency, leaving most of the macromolecule in the loading solution after encapsulation. This may result in significant losses of biologic macromolecules such as proteins during encapsulation. Since recombinant proteins or those isolated from biological sources are expensive to produce, this can add considerable cost to the encapsulation process. The macromolecule solution could potentially be reused multiple times to avoid wasting the macromolecule. However some macromolecules are unstable, especially in solution, and are not amenable to this process.

Some of these problems have been circumvented by the advances disclosed in U.S. Patent Application Publication No. US 2012-0288537 (hereby incorporated by reference in its entirety), including an ionic affinity trap disposed within the microsphere. The described ionic affinity trap can comprise a metal salt such as aluminum hydroxide, aluminum phosphate, potassium phosphate, magnesium carbonate, calcium phosphate or an ionomer gel. Alternatively, the ionic affinity trap can comprise ionized end groups of the polymer, for example, in the case of PLGA, the carboxylate groups of the polymer. The agent to be delivered can comprise a biomolecule, a drug, or an antigen, and include proteins, peptides, proteoglycans, lipoproteins, and nucleic acids. The agent to be delivered can be sorbed to the ionic affinity trap enabling the delivery system to provide higher loading and incorporate a higher level of bioactive agent in the delivery system. Compared to previous delivery systems, these delivery systems achieved elevated loading (>1% w/w) from protein concentrations (<1 mg/ml). Although these advances showed improved encapsulation efficiency of protein antigens and/or loading for bioactive peptides, more efficient loading (e.g., encapsulation efficiency >60%) of pharmaceutical peptides or proteins, and/or elevated protein loading >3% w/w, would be useful for producing certain polypeptide depot formulations (e.g., Bydureon™ and Lupron Depot™, marketed products that have loading of 5% w/w). More efficient loading and/or elevated protein loading would also be particularly useful for early stage research of proposed controlled-release systems, especially when the therapeutic is expensive, not currently produced in large amounts, etc.

It would therefore be desirable to provide a microparticle-based, or similar, controlled delivery system for proteins and other macromolecules, which a) does not expose the active agent to solvents or other harsh conditions during manufacture, b) is capable of loading from aqueous solutions of the active agent at low concentrations, and c) achieves both high loading and high encapsulation efficiency. Additionally, the delivery system would deliver the protein or other macromolecule in its active form over an extended period of time.

SUMMARY

Provided herein are porous self-healing polymer matrices for encapsulation of an active macromolecule, wherein the active macromolecule comprises a peptide or a protein, the matrix comprising a biodegradable polymer and having pores, wherein an ionic affinity trap is disposed within the pores. The ionic affinity trap comprises a metal ion, and the active macromolecule is covalently bound to a histidine tag.

Also provide herein are methods of using a porous self-healing polymer matrix for making a drug delivery system for a macromolecule, the method comprising: loading a macromolecule into the porous self-healing polymer matrix according to the present disclosure by incubating the self-healing polymer matrix in an aqueous solution of the macromolecule wherein the matrix has pores connected to an outer surface of the matrix; and closing the pores and thereby encapsulating the macromolecule within the matrix.

DETAILED DESCRIPTION

Figure 1:
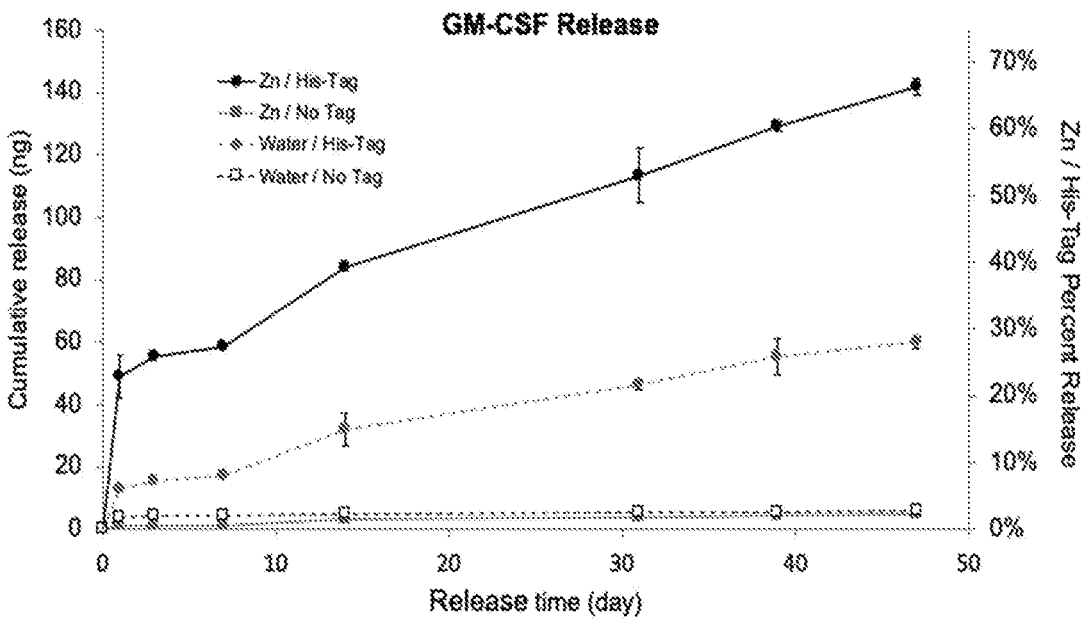
FIG. 1 is a graph of the cumulative release in nanograms of granulocyte-macrophage colony-stimulating factor ("GM-CSF") from a porous self-healing polymer matrix of the present disclosure relative to comparative examples.

The present disclosure is directed to porous self-healing polymer matrices for encapsulation of active macromolecules. The matrices can be used for encapsulating and ultimately delivering active macromolecules including pharmaceutically active agents such as proteins, peptides, and other large molecules. The active macromolecules can be covalently bound to a tag, such as a histidine-tag. The matrix can include a biodegradable polymer and have pores. The porous self-healing polymer matrices can further include an ionic affinity trap disposed within the pores. The ionic affinity trap can include a metal ion.

The present disclosure also relates to methods of using said porous self-healing polymer matrices for making a drug delivery system for a macromolecule. The method can include loading an active macromolecule into the porous self-healing polymer matrix as described herein by incubating said porous self-healing polymer matrix in an aqueous solution of the macromolecule. The matrix has pores connected to an outer surface of the matrix that have access to an external aqueous solution and ultimately can be closed, thereby encapsulating the macromolecule within the matrix.

A major drawback of using certain porous self-healing polymer matrices, such as PLGA, is that the active macromolecules are often exposed to deleterious stresses, including micronization, organic/aqueous interface, shear, and organic solvents, particularly during encapsulation. Remote-loading of the active macromolecules in an aqueous environment and subsequent self-healing of the polymer matrix advantageously bypasses one or more of these destabilizing factors. Current remote-loading strategies, however, generally require specific trapping agent and active macromolecule binding compatibility and, therefore, specific matrix formulations are only useful for loading and encapsulating specific biologic agents. The porous self-healing polymer matrices described herein exploit the non-protein specific binding of metal ions with histidine-tags by incorporating histidine-tags into active macromolecules and immobilizing ionic affinity trap (such as metal ions) in the pores of the self-healing polymer matrix, such that enhanced encapsulation efficiency, and continuous and almost complete cumulative release of the active macromolecule from the porous self-healing polymer matrices is advantageously achieved (at least relative to examples in which the macromolecule does not include a histidine-tag covalently attached thereto). In embodiments, the present disclosure is particularly useful when the availability of the active macromolecule is very low, such as in drug discovery development, when the amount of available macromolecule can be limited. The surprising and unexpected efficient loading of the porous self-healing polymer matrices of this disclosure can be extremely useful for research and development purposes.

Natural and synthetic polymers can be used as the biodegradable polymer herein. In embodiments, the biodegradable polymer can be selected from poly(lactides), poly(glycolides), poly(lactide-co-glycolides), poly (lactic acid)s, poly(glycolic acid)s, poly(lactic acid-co-glycolic acid)s, polycaprolactone, poly(hydroxymethyl glycolide-co-lactide), polycarbonates, polyesteramides, polyanhydrides, poly(amino acids), polyorthoesters, polycyanoacrylates, poly(p-dioxanone), poly(alkylene oxalate)s, biodegradable polyurethanes, homopolymers, copolymers, and blends of these and other polymers can be used to form a porous self-healing polymer matrix. Such porous self-healing polymer matrices are widely used in medical devices and formulations for drug delivery, and are appropriate for various embodiments of the present disclosure. Among these polymers, poly(lactic-co-glycolic acid) ("PLGA")-based polymers possess highly desirable qualities for drug delivery such as biodegradability and biocompatibility. PLGA polymers have been used extensively in microparticles (including microspheres), millicylindrical rods, coatings and various other devices, and their rates of degradation and biocompatibility are well understood.

In one embodiment of the disclosure PLGA is formulated with pore forming agents such as sugars, salts, or any other porosogen to form a self-healing polymer matrix having pores. Suitable sugars include monosaccharides, disaccharides, oligosaccharides, and polysaccharides. An example is trehalose, a disaccharide containing two glucose units. The level of porosogen is selected for forming a suitable pore structure. In various embodiments, the porosogen is provided in the formulation at a level of 1-10%, 1-6%, 1-5%, 2-10%, 2-6%, or 2-5%, for example at about 3% or about 4%, by weight of the biodegradable polymer. In one embodiment of the disclosure, the polymer matrix forms microspheres, and the type and amount of the pore forming agent is selected to form an interconnected pore network within the interior of the microsphere that connects to the exterior surface of the microsphere. This porous network will allow an active macromolecule to penetrate deep into the interior of the microsphere during encapsulation, and to diffuse out of the microsphere through the pore network at an optimal rate during subsequent controlled release.

In embodiments, basic additives or other pH-modifying species can be added into the polymer phase during formation of microspheres to counteract an acidic microenvironment that may develop within the interior porous structure of the microsphere, due to the build-up of acidic degradation products of the polymer in use, especially when used for extended drug delivery. Basic additives appropriate for use in various embodiments of the present disclosure include magnesium carbonate, magnesium hydroxide, magnesium oxide, magnesium trisilicate, zinc carbonate, zinc hydroxide, zinc phosphate, aluminum hydroxide, basic aluminum carbonate, dihydroxyaluminum sodium carbonate, dihydroxyaluminum aminoacetate, calcium phosphate, and calcium hydroxide. In one embodiment of the disclosure a pH modulator is used that has a low aqueous solubility and is a solid within the polymer matrix. In various embodiments, the pH modulator is used at a level of about 1% to about 7% by weight of the biodegradable polymer.

In one embodiment of the disclosure, microspheres are prepared using a double water-oil-water (W/O/W) emulsion of poly(lactic-co-glycolic acid) (PLGA), with $MgCO_3$ or $ZnCO_3$ as a pH modulator, trehalose as a pore forming agent, and in addition, a biopolymer is added during microsphere formation and is incorporated into the interior of the microsphere. As used herein, a "biopolymer" can include an oligosaccharide or a polysaccharide, such as chitosan, a sulfated glycosamino-glycan, a non-sulfated glycosaminoglycan, hyaluronic acid chondroitin sulfate, dextrose sulfate, dextran sulfate, ketran sulfate, heparin, heparin sulfate or combinations thereof.

The porous self-healing polymer matrix of the present disclosure generally include an ionic affinity trap in order to improve the loading and release of the active macromolecule. In embodiments, the ionic affinity trap generally include a metal ion. In embodiments, the metal ion can include a zinc cation, a nickel cation, a cobalt cation, a copper cation, a manganese cation, an iron cation, a chromium cation, or a mixture thereof. In embodiments, the metal ions are selected from $Zn^{2+}$, a $Ni^{2+}$, a $Cu^{2+}$, a $Co^{2+}$, or a mixture thereof. In specific embodiments, the metal ion is $Zn^{2+}$. In other specific embodiments, the metal ion is $Cu^{2+}$.

In embodiments, after the porous microspheres are formed and before the addition of the active macromolecule, the porous microspheres can be incubated in an aqueous solution including an ionic affinity trap at room temperature in a suitable time period for sorbing the ionic affinity trap within the pores, for example from about 1 hour to 72 hours. For example, the incubation period of the porous microspheres with the ionic affinity trap can occur in about 5 hour to about 48 hours, about 10 hours to about 30 hours, or about 12 hour to about 25 hours. In other specific examples, the incubation period can be 1 hour, 2 hours, 3 hours, 4 hours, 5 hours, 10 hours, 15 hours, 20 hours, 24 hours, 30 hours, 35 hours, 40 hours, 50 hours, 60 hours, or 72 hours. During the incubation period, the porous microspheres can immobilize the ionic affinity trap within the pores. In embodiments, a biopolymer can be used to bind to the ionic affinity trap and immobilize the ionic affinity trap within the pores of the porous microspheres.

Desirable characteristics of biopolymers appropriate for use in delivery systems according to the disclosure include the ability to: enhance absorption of the active macromolecular agent of interest from aqueous solution; stabilize the bound active macromolecule; release the bound active macromolecule when the pores of the porous self-healing polymer matrices open; and optionally, provide a synergistic therapeutic effect along with the agent of interest. Suitable biopolymers can include a disaccharide, a trisaccharide, a polysaccharide, or a mixture thereof. In embodiments, the biopolymer can include a polysaccharide. In embodiments, the biopolymers can include chitosan, a sulfated glycosamino-glycan, a non-sulfated glycosamino-glycan, hyaluronic acid, chondroitin sulfate, dextrose sulfate, dextran sulfate, ketran sulfate, heparin, heparin sulfate or combinations thereof. Some of these biopolymers are members of the glycosamino-glycan (GAG) family, or have similar structural moieties (e.g. dextran sulfate). GAGs are polysaccharides that constitute a major portion of the extra cellular matrix, and are therefore biocompatible and non-immunogenic. They are linear, generally sulfated, negatively charged polysaccharides with molecular weights in 10-100 kDa range. Non-sulfated GAGs include hyaluronic acid (HA); sulfated GAGs include chondroitin sulfate (CS), dextran sulfate (DS), ketran sulfate (KS), heparin and heparin sulfate (HP). In various embodiments, the biopolymer is used at a level of at least 0.5%, at least 1%, at least 1.5%, at least 2%, or at least 2.5% by weight of the biodegradable polymer, and at a level below 10%, below 7.5%, below 6%, below 5%, and below 4%, wherein all percentages are by weight of the biodegradable polymer.

In some embodiments of the disclosure, glycosoaminoglycans incorporated into the porous self-healing polymer matrix to help bind and immobilize the protein or other active macromolecule to be delivered by forming a polyelectrolyte complex, and thereby increase loading efficiency of the active macromolecule, and improve the stability of the agent during the encapsulation process and subsequent release of the agent. In one embodiment, the polyelectrolyte complex comprises a positively charged glycosoaminoglycan that binds to one or more negatively charged loci on the protein or other active macromolecule to be delivered from the system. Alternatively, in other embodiments, the polyelectrolyte complex comprises a negatively charged glycosaminoglycan that binds to one or more positively charged loci on the protein or other active macromolecule to be delivered.

In some embodiments of the disclosure the biopolymer/active macromolecule polyelectrolyte complex is present in the interconnected porous system of the microsphere as a non-soluble polyelectrolyte complex, for example, as a coacervate and/or an amorphous precipitate, and therefore when bound in the polyelectrolyte complex, the active macromolecule is inhibited from leaching out of the microsphere during self-healing encapsulation of the macromolecule.

The addition of a biopolymer to the inner water phase of the emulsion during microsphere formation can affect the interconnected pore structure of the microsphere. For example, higher molecular weight hyaluronic acid (HA) (356 or 1010 kDa) has been shown to cause increasing viscosity of the inner water phase of the emulsion and at some HA concentrations, leads to poorly formed primary emulsions, which in turn, leads to deformed microspheres and non-uniform pore structure. In contrast, well-formed HA-PLGA microspheres have been obtained with 66 kDa HA at 2-13% w/w, indicating that both concentration and size of the biopolymer affect pore structure. Therefore, in one embodiment of the disclosure, values for the molecular weight of the biopolymer, the volume of the inner water phase, the PLGA concentration, microsphere size, trehalose or other porosigen loading, and $MgCO_3$ or other pH modifying species loading are selected to obtain well-formed microspheres having an interior space and interconnected pore network suitable to encapsulate and deliver the protein or other active macromolecule of interest.

Ionic interactions govern the specificity of GAG-macromolecule binding and polyelectrolyte complex formation. The polyelectrolyte complex may comprise either a positively charged biopolymer that binds to one or more negative loci of the protein or other negatively charged macromol-ecule, such as DNA, or siRNA. Alternatively, the polyelectrolyte complex may comprise a negatively charged biopolymer capable of binding to positively charged loci on the active macromolecule to be delivered. For example, the carboxylate and sulfate groups of GAG's interact with the basic amino acid residues on a protein agent to enhance binding and thus loading thereof. Thus, the distribution and topology of the basic resides on the GAG dictates the strength and specificity of interactions with positively charged residues on the protein and the stability of the polyelectrolyte complex. In order to achieve strong binding affinity, oligosaccharide sequences on the GAG provide sulfate groups oriented on the surface of the molecule so that they are available for van der Waals-type interactions with basic amino acid residues on the protein. Therefore, the three-dimensional structure and conformation of the GAG plays a crucial role in protein binding. Residues of arginine, lysine and, to a lesser extent, histidine on the surface of the peptide or protein three-dimensional structure are involved in the ionic interactions with highly acidic sulfate groups present on the GAG chains. Binding is also affected by the size of the biopolymer-peptide or biopolymer-protein polyelectrolyte complex. In one embodiment of the disclosure, the interaction between the GAG (or other biopolymer) and the protein (or other macromolecule) is strong enough to immobilize the macromolecule, but also allows the biopolymer-macromolecule polyelectrolyte complex to dissolve, and the agent to diffuse out of the delivery system as the polymer matrix degrades. In one embodiment of the disclosure, the binding constant (k) for the polyelectrolyte complex is in the range of $10^5$ to $10^7$.

In various embodiments, the biopolymer to be used in a biopolymer-PLGA delivery system is a GAG that is selected, based on its both its size and binding affinities for the protein agent to be delivered. In one embodiment of the disclosure, a nonsoluble polyelectrolyte complex forms between the biopolymer and a protein active agent during loading of the agent, is present in the pores of a self-healing polymer matrix, and because it is nonsoluble, restricting mobility of the protein, it does not substantially leach out during loading of the protein and stabilizes the structure of the protein.

In some embodiments of the disclosure, one or more GAGs are selected that stabilize the active macromolecule during the encapsulation process, increase loading of the active macromolecule into the porous biopolymer-PLGA micro spheres, and release the active macromolecule under physiological conditions. In some embodiments of the disclosure, such a delivery system provides a means of delivering an active macromolecule for an extended period of greater than 40 days. For example, high molecular weight dextran sulfate (approximately 500 kDa) added to PLGA formulations have been shown to control release of lysozyme (LYZ) from the PLGA microspheres by reducing initial burst. In addition the rate of LYZ release could be adjusted by changing the HDS:active macromolecule ratio during encapsulation. Further, the high molecular weight of HDS minimizes potential leaching and complications during encapsulation of proteins, and results in high loading and encapsulation efficiency, and thereby reduces losses of expensive recombinant proteins during encapsulation. These encapsulation and release characteristics demonstrate that HDS-PLGA microspheres advantageously provide long-acting-release formulations.

In embodiments, as mentioned above, the porous self-healing polymer matrix can further include a biopolymer disposed within the pores of the biodegradable polymer. The biopolymers within the matrix can bind, sequester, and stabilize the active macromolecule that is ultimately loaded into the porous self-healing polymer matrix. In some embodiments the biopolymers enhance the biological effect(s) of the active macromolecules, such as a protein, by acting as co-factors. In other embodiments the biopolymers stabilize the active macromolecules by enhancing immobilization thereof in a manner similar to how a physiological extracellular matrix stabilizes the structure of growth factors upon binding. In one embodiment of the disclosure biopolymers are selected that act as binding agents for the active macromolecule to be delivered in order to enhance the efficiency of loading and microencapsulation of the active macromolecule in the porous microspheres.

The active macromolecule to be encapsulated may include a peptide, a protein, a nucleic acid, DNA, siRNA, or other large molecule. In embodiments, the active macromolecule can be a protein, a peptide, or a mixture thereof. In some embodiments the molecular weight of the active macromolecule is >1000 kDa. As used herein, "active macromolecule" refers to a macromolecule exhibiting a therapeutic effect. A therapeutic effect refers to the treatment of disease or disorders by remedial agents or methods.

In the present disclosure, the active macromolecule includes a tag covalently bound to the active macromolecule. Generally, the tag is included because it functions as an affinity tag capable of binding with a metal ion of an ionic affinity trap immobilized within the microsphere pores, for example, through coordination or chelation. Thus, the tag is typically selected based on the tag's affinity for the ionic affinity trap that is selected. The tag according to the disclosure typically includes more than one histidine residues and thus can be referred to as a polyhistidine tag. For example, the polyhistidine tag can include 2, 3, 4, 5, 6, 7, 8, 9, 10, 11, 12, 13, 14, or 15 histidine residues. In specific non-limiting embodiments, the histidine tag can include 6 to 9 histidine residues. In one example, the histidine-tag is a hexahistidine tag (commonly referred to as "His-tag" in the art).

The active macromolecule can be genetically modified to include the aforementioned tag for binding to the ionic affinity trap. In embodiments, the active macromolecule can be genetically modified to include one or more polyhistidine tags at the C-terminus, at the N-terminus, or at both terminuses. Thus, the active macromolecule can include one histidine tag at the C-terminus, one histidine tag at the N-terminus, or two histidine tags at both the N-terminus and the C-terminus of a given active macromolecule.

The ionic affinity traps within the pores of the porous microspheres provide coordination sites for both the active macromolecule and the histidine tag on the active macromolecule. The affinity of the histidine tag of the active macromolecule for the ionic affinity traps is high when the ionic affinity trap includes a metal ion including a zinc cation, a nickel cation, a cobalt cation, or a copper cation. The interaction between the histidine tag and the ionic affinity trap is generally a metal coordination interaction and not simply an ionic interaction. Due to the strong nature of this interaction, the porous self-healing polymer matrices of the present disclosure exhibit advantageously high encapsulation efficiencies of the active macromolecule. Further, the porous self-healing polymer matrices of the present disclosure exhibit continuous and almost complete release of the active macromolecule. As the coordination between the ionic affinity trap and the histidine tag is not predominantly ionic in nature, the affinity between the two will be high irrespective of the native or final charge of the active macromolecule.

Active macromolecule encapsulation by preformed porous PLGA microspheres is a two-step process consisting of a loading phase followed by pore closure, although some pore closing may occur during the loading phase and some loading may occur in the pore closure phase. Optimal encapsulation conditions generally require the lowest temperature and duration at which a majority of surface pores close while encapsulating the maximum amount of active macromolecule from the loading solution. In some embodiments of the disclosure, optimal results were achieved when the PLGA microspheres were incubated in an aqueous solution with an ionic affinity trap at room temperature for 24 hours followed by incubating porous PLGA microspheres in a solution of active macromolecule including a polyhistidine tag with 6 or more histidine residues for 48 hours at 24° C. Healing is also beneficial to the polymer matrix after encapsulation because it allows the polymer chains to reach a lower energy state when in contact with water, which should minimize physical aging of the polymer during storage. Physical aging can undesirably increase initial burst release. A self-healing polymer matrix can potentially be healed in numerous ways including external stimuli that result in mobilization of the surface polymer chains that causes them to undergo rearrangement to minimize the interfacial tension or other residual stresses in the polymer and thereby to heal the pore or defect. Healing could also be done in air if the temperature is raised above the relevant $T_g$ of the polymer, e.g., wet or dry $T_g$ depending on whether the polymer is hydrated or not.

One embodiment of the disclosure includes a method of manufacturing a drug delivery system for a macromolecule such as a protein, peptide, DNA, siRNA or other large molecules (i.e., roughly >1000 Da). First, using a double water-oil-water (W/O/W) emulsion, PLGA is formulated with one or more pore forming agents, a pH modulator such as $MgCO_3$ or $ZnCO_3$, and a biopolymer that is added to the inner water phase of the emulsion during microsphere formation and incorporated into the pores of the microsphere. The resulting porous microspheres have an interconnected pore network that will allow an active macromolecule that is to be delivered to penetrate deep into the interior of microsphere during encapsulation, and to diffuse out of the microsphere through the interconnected pore network at an optimal rate during subsequent controlled release.

Next, the porous microspheres are incubated with an ionic affinity trap in an aqueous phase. This allows the affinity trap to be immobilized in the porous microspheres for optimal coordination to the active macromolecule. Thus, the biopolymer and ionic affinity trap are selected to achieve sufficient binding affinity with the active macromolecule to be encapsulated efficiently and/or to achieve other desired characteristics (high loading and/or improved protein stability, release, or activity). In addition, the molecular weight of the biopolymer, the volume of the inner water phase of the water-oil-water emulsion, the biodegradable polymer (e.g., PLGA) concentration, microsphere size, concentration of pore forming agent, and pH modifying agent loading are selected to obtain well-formed microspheres suitable to deliver the active macromolecule of interest.

Subsequently, the active macromolecule is loaded into the preformed PLGA microspheres by incubating the microspheres in a solution of the macromolecule. The macromolecule diffuses into the microsphere where it binds to the ionic affinity agent within the pores of the microsphere via the histidine tag. Binding to the ionic affinity trap immobilizes the active macromolecule to be delivered, and thereby increases loading efficiency of the active macromolecule, and improves the stability of the active macromolecule during the encapsulation process and subsequent release of the active macromolecule. The percent w/w load of the active agent is quantified as:

(mass of protein encapsulated in microspheres/total mass of microspheres in loading solution)×100.

The percentage encapsulation efficiency is calculated as:

(mass of protein encapsulated in microspheres/total mass of protein in loading solution)×100.

In embodiments, the encapsulation efficiency of the porous self-healing polymer matrix as disclosed herein can be at least 35%, at least 40%, at least 45%, at least 50%, at least 55%, at least 60%, at least 65%, at least 70% or at least 75%. In embodiments, the encapsulation efficiency of the porous self-healing polymer matrix as disclosed herein is at least 35%. In embodiments, the encapsulation efficiency of the porous self-healing polymer matrix as disclosed herein is at least 50%. In embodiments, the encapsulation efficiency of the porous self-healing polymer matrix as disclosed herein is at least 70%.

Finally, the porous self-healing polymer matrices are incubated in an aqueous solution at a temperature above the $T_g$ so that the pores on the surface of the microsphere close (heal), encapsulating the active macromolecule. In one embodiment PLGA microspheres have a hydrated glass transition temperature of well below 43° C., a temperature at which many macromolecules, including proteins are stable for sufficient periods of time to allow pore healing. However, in some embodiments, plasticizers are added to the PLGA to further reduce the healing temperature to 37° C. Alternatively, in other embodiments, different methods can be used to close the pores besides temperature change. For example, exposure to a solvent, such as alcohol vapor, can be used to facilitate pore closure (self-healing) of the polymer matrix. A self-healing polymer matrix can potentially be healed in numerous other ways including external stimuli that result in mobilization of the surface polymer chains that causes them to undergo rearrangement to minimize the interfacial tension or other residual stresses in the polymer and thereby to heal the pore or defect. Healing could also be done in air if the temperature is raised above the relevant $T_g$ (wet or dry) of the polymer.

Loading the active macromolecule into preformed microspheres and associating (binding) the active macromolecule with a biopolymer and/or the ionic affinity trap within the microsphere, as disclosed herein, provides a delivery system exhibiting high loading and encapsulation efficiency of the macromolecular agent, a desirable release profile, and stability for an extended time period.

The following examples are included to demonstrate preferred embodiments of the invention. It should be appreciated by those of skill in the art that the techniques disclosed in the following examples represent techniques that function well in the practice of the invention, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the invention.

The use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict embodiments for purposes of illustration only. One of ordinary skill in the art will readily recognize from the following discussion that alternative embodiments of the structures and methods illustrated herein may be employed without departing from the principles described herein.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Materials

RG 504 poly(lactic-co-glycolic) acid (PLGA) (inherent viscosity 0.45-0.60 dL/g, molecular weight 38-54 kDa, 50:50, ester-terminated) was purchased from Sigma-Aldrich. D-(+)-Trehalose dihydrate was purchased from Alfa Aesar (Heysham, Lancashire, England). High molecular weight (>500 kDa) dextran sulfate (HDS) sodium salt and magnesium chloride ($MgCO_3$) were purchased from Sigma-Aldrich. Methylene Chloride (DCM) was purchased from Fisher Scientific. A Tempest I.Q.$^2$ microprocessor homogenizer from Sentry was used for homogenization and a Eurostar 20 digital overhead stirrer from IKA was used for stirring. Zinc acetate (ZnAc), calcium acetate, (CaAc), copper acetate (CuAc), cobalt acetate (CoAc), nickel acetate (NiAc), and sodium acetate (NaAc) were purchased from Sigma-Aldrich, and sodium chloride (NaCl) was purchased from Fisher Scientific. Phosphate buffered saline (PBS) (10×) was purchased from Gibco and diluted and pH-adjusted as directed. Bovine serum albumin (BSA) was purchased from Sigma-Aldrich. Granulocyte macrophage colony-stimulating factor (GM-CSF) was purchased from ProSpec Protein Specialists. Human GM-CSF Standard ABTS ELISA Development Kit was purchased from PeproTech. Insulin-like growth factor-1 (IGF-1) was purchased from Signalway Antibody. Human IGF-1 ELISA was purchased from RayBiotech. Human Serum Albumin (HSA) was purchased from antibodies-online. Coomassie Plus reagent was purchased from ThermoFisher Scientific. Inductively-Coupled Plasma—Mass Spectrometry (ICP-MS) was conducted using an PerkinElmer ICP-MS.

Example 1

250 mg of PLGA and 6% $MgCO_3$ (w/w of formulation) were placed in a 16 mm glass cell culture tube. 1 mL dichloromethane (DCM) was added, the tube was closed with a rubber stopper, and the tube was vortexed briefly. The tube was then shaken at 120 rpm for 1 hour. 150 mL of 0.5%

PVA in a 250 mL beaker was placed on a stir plate in a chemical hood such that the swirl vortex reached halfway from the surface to the bottom of the beaker. The inner water phase of 4% HDS (w/w of formulation) and 3% trehalose (w/w of formulation) was dissolved in 200 μL ddH$_2$O (double-distilled water). The tube of PLGA was removed from the shaker and briefly vortexed. The 200 μL inner water phase was added to the center of the PLGA tube. The tube was placed in an ice bath and homogenized at 18 krpm for 1 min. 2 mL of 5% PVA was added to the tube. The tube was vortexed strongly for 1 minute. The tube contents were immediately poured into the stirring 0.5% PVA. The beaker was stirred for 3 hours. The contents of the beaker were sieved to collect the 20-63 μm microsphere fraction. 1 L of ddH$_2$O was poured through the 20 μm sieve to wash the microspheres. The microspheres were collected in a 50 mL polypropylene tube and centrifuged for 5 minutes at 1000 g. The water supernatant was discarded and the microspheres were freeze-dried for 48 hours.

Example 2

Remote loading and release: 1 mg (+/−0.05 mg) of drug-free PLGA microspheres prepared according to Example 1 was weighed into each of eight 2 mL eppendorf tubes (n=2 for each of Zn/His-Tag, Zn/No Tag, Water/His-Tag, and Water/No Tag). Four experiments were run, the first labeled "Zn/His-Tag", the second labeled "Zn/No Tag", the third labeled "Water/His-Tag", and the fourth labeled "Water/No Tag". The Zn/His-Tag experiment represents the porous self-healing polymer matrices of the present disclosure, where the Zn is a Zn$^{2+}$ cation and is used as the ionic affinity trap, and the active macromolecule includes a polyhistidine tag. The other three experiments represent comparative examples, i.e. Zn/No Tag (the active macromolecule does not include a polyhistidine tag, but an ionic affinity trap with affinity for a histidine tag as disclosed herein was included), Water/His-Tag (no ionic affinity trap with affinity for a histidine tag as disclosed herein was included but a polyhistidine tag is present on the active macromolecule), and Water/No-Tag (no ionic affinity trap with affinity for a histidine tag as disclosed herein and no polyhistidine tag was included on the active macromolecule). The term "His-tag", referred to herein is a hexahistidine tag.

For the experiments with the Zn ionic affinity trap, the microspheres were incubated in 1 mL of 100 mg/mL ZnAc or double-distilled water (ddH$_2$O) for 24 hr at room temperature, rotating at 25 rpm. The microspheres were then washed twice with 1 mL ddH$_2$O by centrifuge at 8000 rpm for 5 minutes. To load the drug (IGF-1), the microspheres were incubated in 0.1 mL of 50 μg/mL His-tagged or untagged drug in 50 mM NaAc, 300 mM NaCl, pH 8 for 48 hours at room temperature, rotating at 25 rpm (for the experiments without the Zn affinity tag, the experiment starts with this step). To load the drug (GM-CSF), the same conditions were used as the IGF-1 loading except the concentrations were different. The initial concentrations for the Zn/No Tag and the water/No Tag experiments were 15.86 μg/mL. The initial concentrations for the Zn/His-Tag and water/His-Tag experiments were 5.80 μg/mL. Desalting columns were used to change the buffer of GM-CSF. IGF-1 was diluted in the loading solution. To induce pore-closure, microspheres were incubated for 42 hours at 43° C., rotating at 25 rpm. Microspheres were centrifuged for 5 min at 8000 rpm and the supernatant was removed and kept for loading tests. Microspheres were washed with 1 mL ddH$_2$O by centrifuge at 8000 rpm for 5 min and freeze-dried for 48 hours. Microspheres were incubated in 1 mL PBS+0.02% Tween 80+1% BSA at 37 QC, shaking at 240 rpm for release. Time-points were taken by centrifuging the microspheres for 5 min at 8000 rpm, removing and keeping the supernatant for release testing, and completely replacing the media. Time-points were taken at 1 day, 3 days, 7 days, and weekly thereafter.

The initial starting drug mass loading solutions was 5 microgram for 1 mg microspheres. The loading results based on mass percentage are below:

|  | GM-CSF % | IGF-1% |
|---|---|---|
| Zn/His-Tag | 0.214% | 0.444% |
| Zn/No Tag | 0.426% | 0.080% |
| Water/His-Tag | 0.040% | 0.207% |
| Water/No Tag | 0.137% | 0.127% |

Loading results in terms of encapsulation efficiencies are shown in the table below:

|  | GM-CSF - *EE | IGF-1 - *EE |
|---|---|---|
| Zn/His-Tag | 74.56% | 88.87% |
| Zn/No Tag | 27.59% | 15.99% |
| Water/His-Tag | 13.94% | 41.35% |
| Water/No Tag | 8.87% | 25.38% |

*EE = encapsulation efficiency

Quantification: The amount of drug loaded into the microspheres was determined by mass loss of drug from the loading solution. The loading solutions used in the experiments were compared to loading solutions that had not yet been used for loading (see Remote-loading and release above). Drug concentrations were quantified using the appropriate ELISA kit and by executing the included protocols. The same His-Tag and No Tag Human GM-CSF and IGF-1 used in the experiments were used as standards in lieu of the kit standards. For IGF-1, the initial concentration of drug in the loading solution was assumed to be 50 μg/mL based on dilutions.

Figure 2:
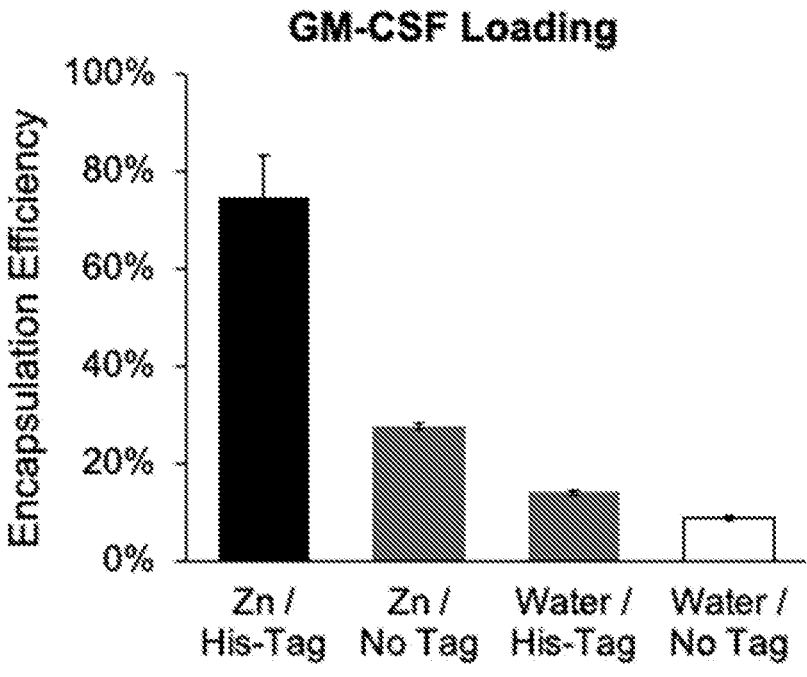
FIG. 2 is a graph of the loading (based on the encapsulation efficiency in %) of GM-CSF in the porous self-healing polymer matrix of the present disclosure relative to comparative examples.
Figure 3:
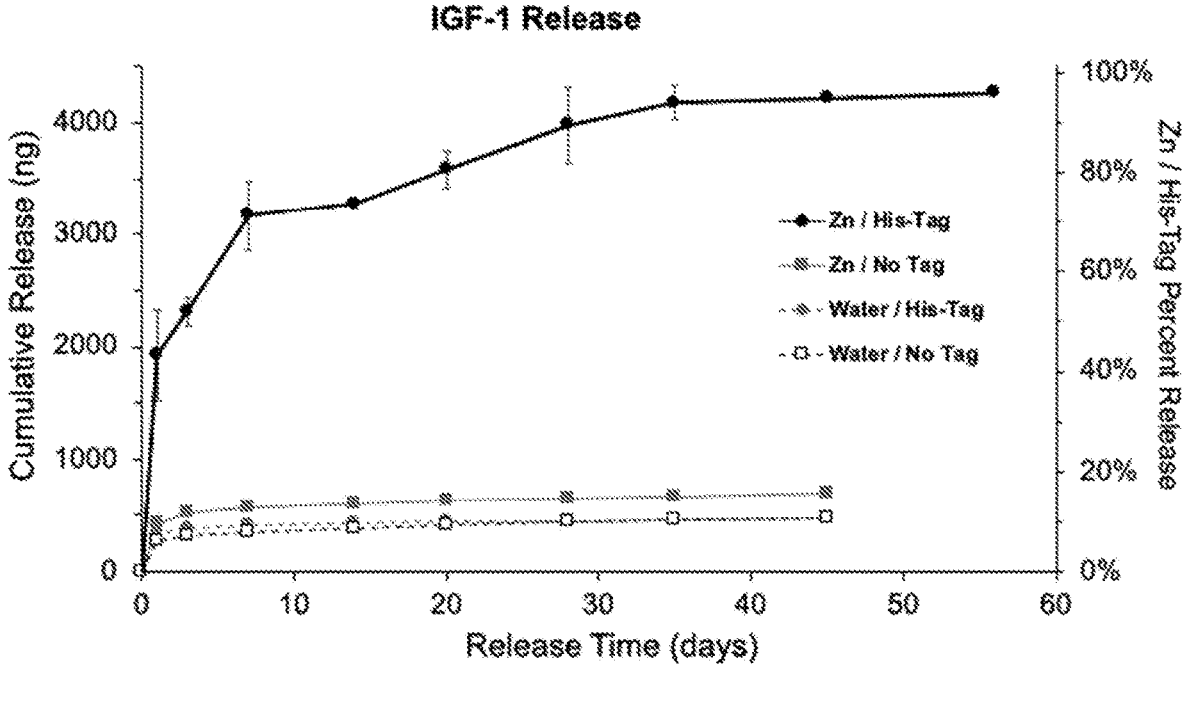
FIG. 3 is a graph of the cumulative release in nanograms of insulin-like growth factor 1 ("IGF-1") from a porous self-healing polymer matrix of the present disclosure relative to comparative examples.
Figure 4:
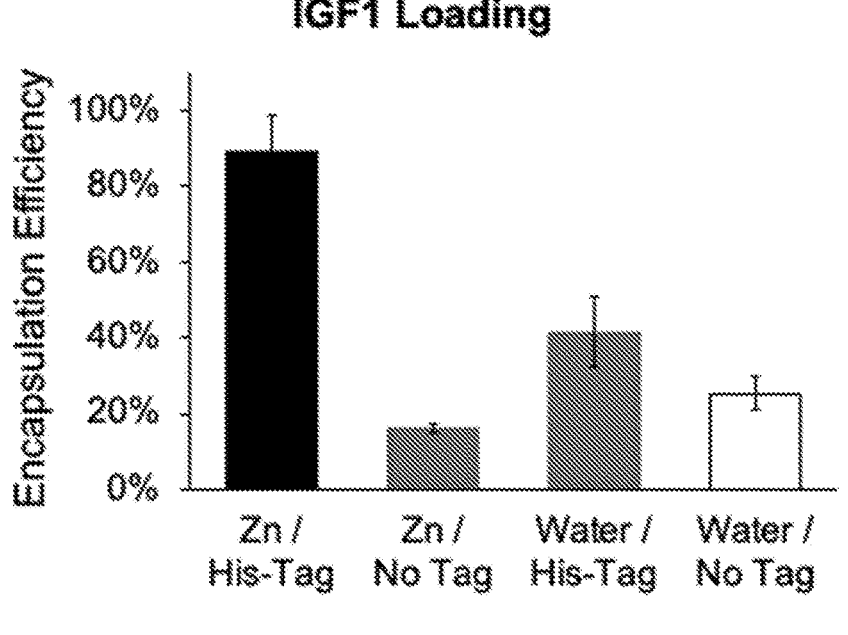
FIG. 4 is a graph of the loading (based on the encapsulation efficiency in %) of IGF-1 in the porous self-healing polymer matrix of the present disclosure relative to comparative examples.

The closest prior art to the present disclosure, consistent with the teachings of US 2012/0288537 A1, is exemplified by the experiment labeled as Zn/No-Tag. Another comparative example is used consistent with the teachings of US Patent Publication No. 2015/0164805 A1, and is exemplified by the experiment labeled as Water/No-Tag in Example 2. However, the addition of an ionic affinity trap including a metal ion including Zn$^{2+}$, Ni$^{2+}$, Cu$^{2+}$, Ca$^{2+}$, or Co$^{2+}$, in combination with a His-tag on the active macromolecule of interest, such as IGF-1 and GM-CSF shown above, clearly results in markedly better encapsulation efficiencies of the active macromolecule (FIGS. 2 and 4) and particularly advantageous cumulative release of the active macromolecule (FIGS. 1 and 3). The release curves in FIGS. 1 and 3, show continuous release of the drug over time, and almost all of the drug present in the porous self-healing polymer matrices is released. The porous self-healing polymer matrices of the present disclosure using both IGF-1 and GM-CSF have shown the best release kinetics of an active macromolecule from a PLGA microsphere that is known to date.

Example 3

Metal Comparison: Drug-free PLGA microspheres were rotated in 500 mM (or saturated solutions in the case of copper) calcium acetate, cobalt acetate, copper acetate, nickel acetate, zinc acetate, or ddH$_2$O (alone) at 30 rpm for 24 hours. Microspheres were washed with ddH$_2$O by vacuum filtration and lyophilized. The amount of metal ion loaded into the microspheres was determined by ICP-MS. At least 3 experiments were conducted for each metal and for water as a control, as follows: 1 mg of microspheres was weighed into 2 mL eppendorf tubes. HisTag IGF-1 was diluted in loading buffer and was loaded into the microspheres as described above. Loading and encapsulation efficiency were determined by drug concentration change in the loading solution as measured by ELISA and Coomassie. Encapsulation advantage was defined as the difference in encapsulation efficiency between a formulation with a metal in the microspheres and the encapsulation efficiency of the "water" (metal-free) microspheres. The metal-normalized encapsulation advantage was determined by dividing the encapsulation advantage for a given formulation by the metal loading for that formulation.

The metal loading percents by mass % are shown in the table below:

| Metal Comparison - Metal Loading | | |
| --- | --- | --- |
| | Loading | Standard Deviation |
| Ca | 0.66% | 0.05% |
| Co | 0.17% | 0.05% |
| Cu | 0.16% | 0.05% |
| Ni | 0.24% | 0.03% |
| Zn | 0.32% | 0.01% |

The metal loading results in terms of encapsulation efficiencies are shown in the table below:

| Metal Comparison - Encapsulation Efficiency | | |
| --- | --- | --- |
| | Mean | Standard Deviation |
| Ca | 36.21% | 5.08% |
| Co | 51.22% | 4.40% |
| Cu | 76.53% | 2.89% |
| Ni | 60.95% | 2.58% |
| Zn | 83.32% | 1.59% |
| Water | 31.49% | 1.68% |

The encapsulation advantage is the encapsulation efficiency of each metal minus the encapsulation efficiency of the comparative example (water). The results are shown in the table below:

| Metal Comparison - Encapsulation Advantage | | |
| --- | --- | --- |
| | Mean | SD |
| Ca | 4.72% | 5.08% |
| Co | 19.73% | 4.40% |
| Cu | 45.04% | 2.89% |
| Ni | 29.47% | 2.58% |
| Zn | 51.83% | 1.59% |

The metal normalized encapsulation advantage results are in the table below:

| Metal Comparison - Metal Normalized Encapsulation Advantage | | |
| --- | --- | --- |
| | Mean | SD |
| Ca | 0.03% | 0.03% |
| Co | 0.66% | 0.13% |
| Cu | 1.83% | 0.17% |
| Ni | 0.71% | 0.06% |
| Zn | 1.08% | 0.03% |

Figure 5:
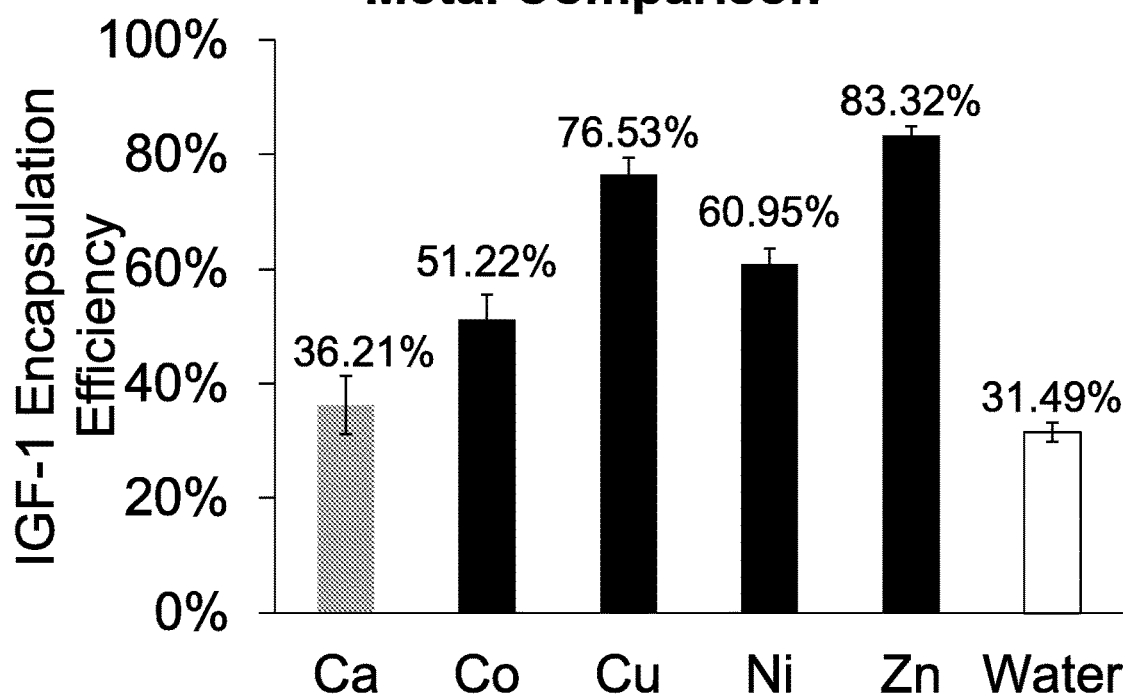
FIG. 5 is a graph of the loading (based on the encapsulation efficiency in %) of IGF-1 in porous self-healing polymer matrices of the present disclosure relative to a comparative example.
Figure 6:
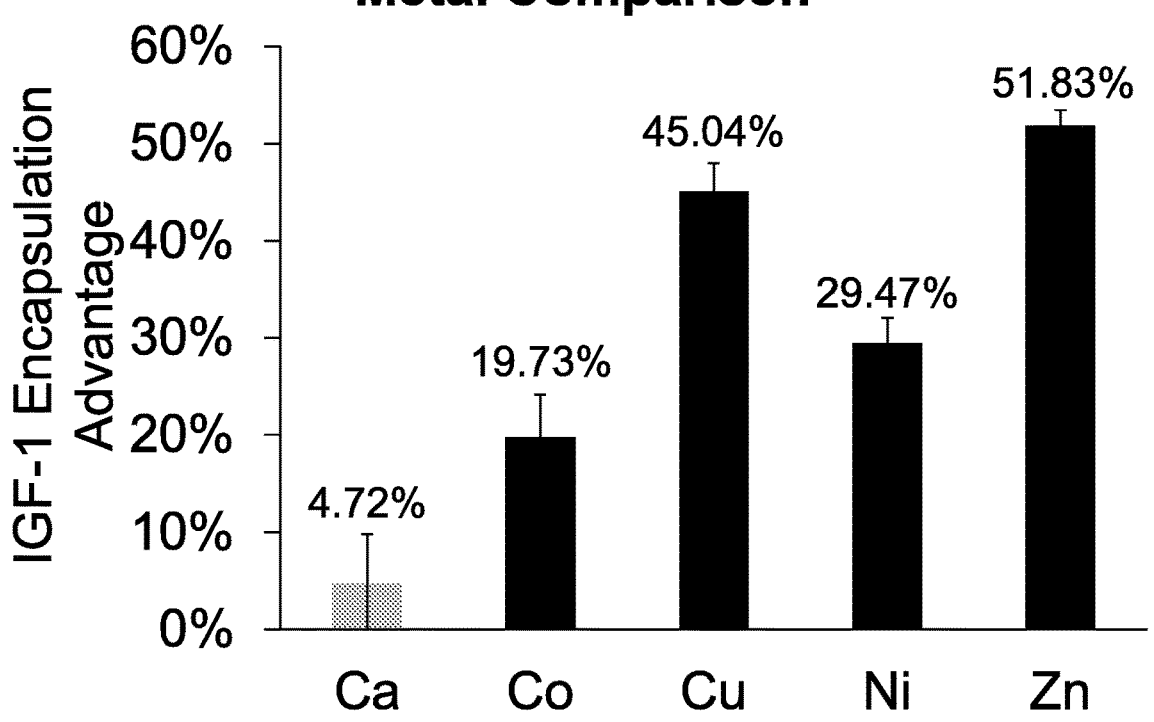
FIG. 6 is a graph of the encapsulation advantage (i.e., the encapsulation efficiency of each self-healing polymer matrix including a metal less the encapsulation efficiency of the comparative example [water]) of IGF-1 in the porous self-healing polymer matrices of the present disclosure.
Figure 7:
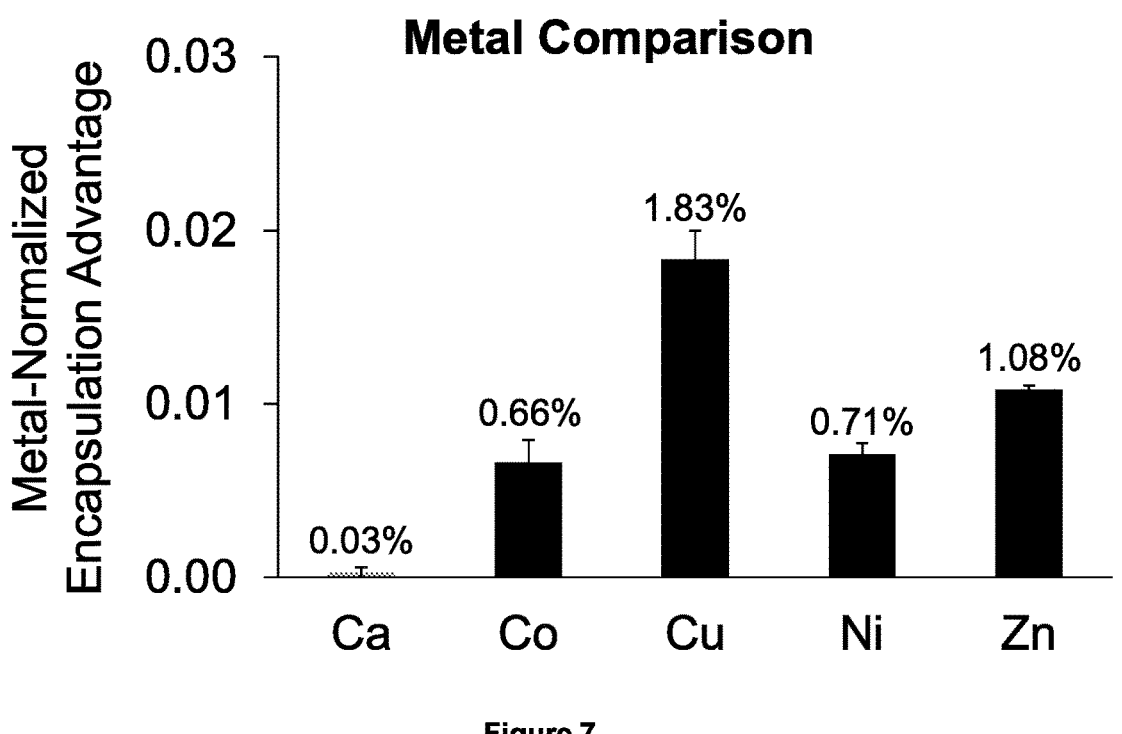
FIG. 7 is a graph of the metal normalized encapsulation advantage per nanomole of metal loaded into the microspheres for IGF-1 in the porous self-healing polymer matrices of the present disclosure.
Figure 8:
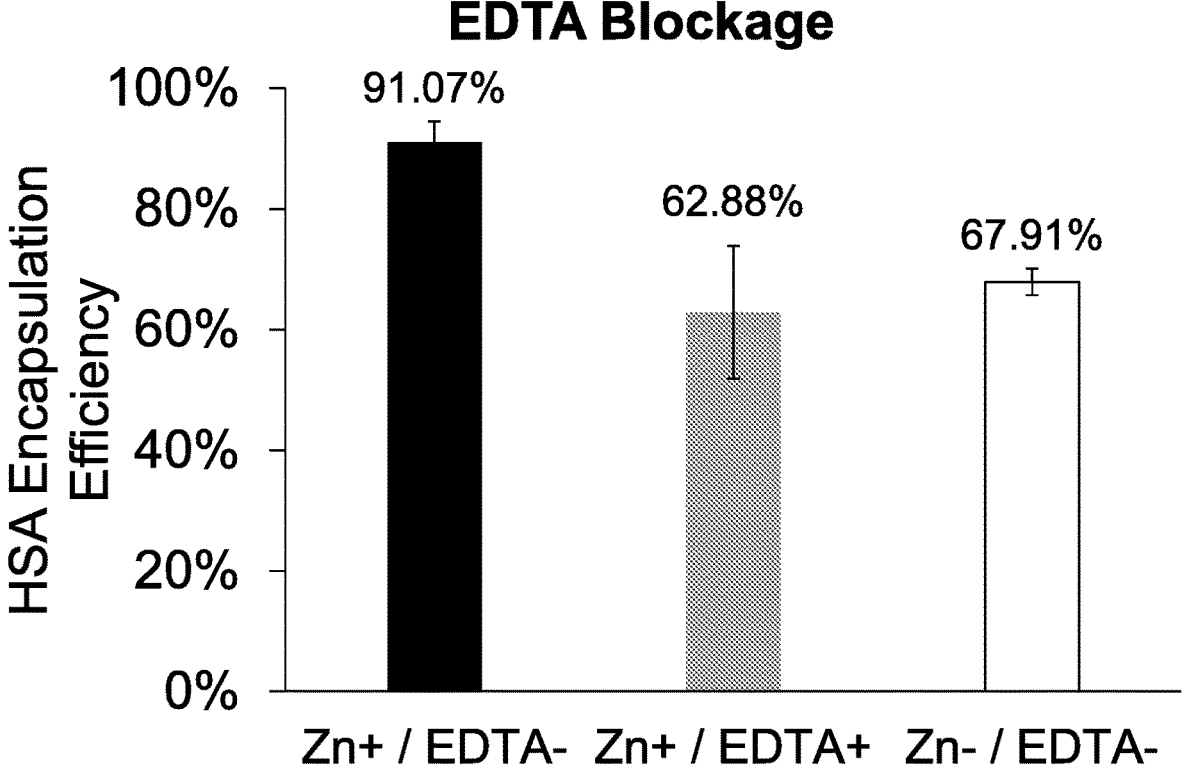
FIG. 8 is a graph of the loading (based on the encapsulation efficiency in %) of human serum albumin (HSA) wherein zinc is present and 2,2',2'',2'''-(Ethane-1,2-diyldinitrilo)tetraacetic acid (EDTA) is absent (left), zinc and EDTA are present (middle) and nether zinc nor EDTA are present in the porous self-healing polymer matrix of the present disclosure.

The closest prior art to the present disclosure, consistent with the teachings of US Patent Publication No. 2015/0164805 A1, is exemplified by the experiment labeled as Water in Example 3. However, the addition of an ionic affinity trap including a metal ion including Zn$^{2+}$, Ni$^{2+}$, Cu$^{2+}$, or Co$^{2+}$, in combination with a His-tag on the active macromolecule of interest, such as IGF-1 shown above, clearly results in markedly better encapsulation efficiencies of the active macromolecule (FIG. 5-7). In particular, FIG. 7 shows the encapsulation advantage gained per unit metal loaded into the microspheres. The y-axis is encapsulation advantage (previously described) per nanomole of metal loaded into the microspheres. Different amounts of the respective metals were loaded into the microspheres, so this graph controls for that in comparing the metals. Copper is by far the best at nearly 2%. Additionally, the encapsulation advantage offered by Calcium is almost non-existent, which fits with the hypothesis that this is metal coordination-driven loading, as calcium is known to be less able to form metal coordination bonds with histidine.

Example 4

EDTA blockage: As a strong chelator, EDTA should interfere with the coordination interaction between histidine tags and metal ions. To probe whether HisTag-metal coordination was driving the increase in encapsulation efficiency, microspheres loaded with zinc as described above (or ddH$_2$O as a control) were rotated in 50% saturated EDTA in water (or ddH$_2$O as a control) for 24 hours at room temperature and were then lyophilized. HisTag HSA was buffer exchanged into loading buffer using Amicon ultrafiltration filters and loaded into the microspheres as described above. Loading and encapsulation efficiency were determined by drug concentration change in the loading solution as measured by Coomassie.

The results of the EDTA blockage on Zn metal is shown in the table below:

| EDTA Blockade | | |
| --- | --- | --- |
| | Mean | SD |
| Zn+/EDTA+ | 62.88% | 11.06% |
| Zn+/EDTA− | 91.07% | 3.44% |
| Zn−/EDTA− | 67.91% | 2.20% |

This example shows that a strong chelating agent (EDTA) can block the ability of the encapsulated metal to form coordination bonds with the HisTags. Zn-loaded microspheres placed in an EDTA loading solution and then in solution of HisTagged Human Serum Albumin were prevented from loading the active macromolecule because the metal coordination sites were occupied by EDTA, again confirming that drug loading was driven by metal-coordination interactions.

What is claimed:

1. A porous self-healing polymer matrix encapsulating an active macromolecule, comprising:
   a porous self-healing polymer matrix comprising a biodegradable polymer and having pores; and,
   an active macromolecule comprising a peptide or a protein; and
   an ionic affinity trap disposed within the pores;
   wherein the ionic affinity trap comprises a metal ion, and
   wherein the active macromolecule is covalently bound to a histidine tag.

2. The porous self-healing polymer matrix of claim 1 wherein the biodegradable polymer is selected from poly (lactides), poly(glycolides), poly(lactide-co-glycolides), poly(lactic-acid)s, poly(glycolic acid)s, poly(lactic acid-co-glycolic acid)s, poly(hydroxymethyl glycolide-co-lactide), polycaprolactone, polycarbonates, polyesteramides, polyanhydrides, poly(amino acids), polyorthoesters, polycyanoacrylates, poly(p-dioxanone), poly(alkylene oxalate)s, and polyurethanes.

3. The porous self-healing polymer matrix of claim 2 wherein the biodegradable polymer comprises poly(lactic-co-glycolic acid).

4. The porous self-healing polymer matrix of claim 1 further comprising a biopolymer disposed within the pores of the biodegradable polymer.

5. The porous self-healing polymer matrix of claim 4, wherein the biopolymer comprises a polysaccharide.

6. The porous self-healing polymer matrix of claim 5, wherein the active macromolecule comprises a net positively charged macromolecule.

7. The porous self-healing polymer matrix of claim 6, wherein the biopolymer comprises a negatively charged polysaccharide.

8. The porous self-healing polymer matrix of claim 5, wherein the active macromolecule comprises a net negatively charged macromolecule.

9. The porous self-healing polymer matrix of claim 8, wherein the biopolymer comprises a positively charged polysaccharide.

10. The porous self-healing polymer matrix of claim 5, wherein the polysaccharide comprises chitosan, a sulfated glycosamino-glycan, a non-sulfated glycosamino-glycan, hyaluronic acid chondroitin sulfate, dextrose sulfate, dextran sulfate, ketran sulfate, heparin, heparin sulfate or combinations thereof.

11. The porous self-healing polymer matrix of claim 10, wherein the polysaccharide comprises dextran sulfate.

12. The porous self-healing polymer matrix of claim 1, wherein the metal ion comprises a zinc cation, a nickel cation, a cobalt cation, a copper cation, a manganese cation, an iron cation, a chromium cation, or a mixture thereof.

13. The porous self-healing polymer matrix of claim 12, wherein the metal ion comprises $Zn^{2+}$.

14. The porous self-healing polymer matrix of claim 12, wherein the metal ion comprises $Cu^{2+}$.

15. The porous self-healing polymer matrix of claim 4, wherein the metal ion is capable of binding both the histidine tag and the biopolymer.

16. A method of manufacturing a porous self-healing polymer matrix encapsulating an active macromolecule according to claim 1, the method comprising:
   loading the active macromolecule into the porous self-healing polymer matrix by incubating the porous self-healing polymer matrix, the self-healing polymer matrix comprising the biodegradable polymer and having pores, the ionic affinity trap being disposed within the pores, in an aqueous solution of the active macromolecule, the active macromolecule comprising the peptide or the protein and being covalently bound to the histidine tag, wherein the pores are connected to an outer surface of the matrix; and closing the pores and thereby encapsulating the active macromolecule.

17. The method of claim 16, wherein the active macromolecule is a net positively charged peptide or a net positively charged protein.

18. The method of claim 16, wherein the porous self-healing polymer matrix further comprises a biopolymer disposed within the pores of the biodegradable polymer, the biopolymer comprises a polysaccharide, and the polysaccharide comprises chitosan, a sulfated glycosamino-glycan, a non-sulfated glycosamino-glycan, hyaluronic acid chondroitin sulfate, dextrose sulfate, dextran sulfate, ketran sulfate, heparin, heparin sulfate or combinations thereof.

19. The method of claim 18, wherein the polysaccharide comprises dextran sulfate.

20. The method of claim 16, wherein an encapsulation efficiency of protein is at least 35%.

21. The method of claim 16, wherein an encapsulation efficiency of protein is at least 50%.

* * * * *